United States Patent
Sugiyama et al.

[11] Patent Number: 5,804,699
[45] Date of Patent: Sep. 8, 1998

[54] AIR-FUEL RATIO SENSOR UNIT

[75] Inventors: Tomio Sugiyama, Nagoya; Makoto Nakae, Toyoake, both of Japan

[73] Assignee: Nippondenso Co., Ltd., Kariya, Japan

[21] Appl. No.: 659,532

[22] Filed: Jun. 6, 1996

[30] Foreign Application Priority Data

Jun. 7, 1995 [JP] Japan ................................ 7-166982

[51] Int. Cl.⁶ ........................................ G01N 27/58
[52] U.S. Cl. ........................................ 73/23.32
[58] Field of Search ...................... 73/23.31, 23.32, 73/116, 117.2, 117.3, 118.1; 364/431.062

[56] References Cited

U.S. PATENT DOCUMENTS

| | | | |
|---|---|---|---|
| 4,454,494 | 6/1984 | Williams et al. | 73/23.32 |
| 4,535,316 | 8/1985 | Wertheimer et al. | 73/23.32 |
| 4,570,479 | 2/1986 | Sakurai et al. | 73/116 |
| 4,712,419 | 12/1987 | Ikai et al. | 73/116 |
| 4,784,743 | 11/1988 | Iino et al. | 204/425 |
| 4,909,072 | 3/1990 | Logothetis et al. | 73/116 |
| 5,231,864 | 8/1993 | Ishida et al. | 73/23.32 |
| 5,288,389 | 2/1994 | Yamada et al. | 204/425 |

FOREIGN PATENT DOCUMENTS

| | | |
|---|---|---|
| 60-111151 | 6/1985 | Japan . |
| 1-206255 | 8/1989 | Japan . |
| 1-272955 | 10/1989 | Japan . |

*Primary Examiner*—George M. Dombroske
*Attorney, Agent, or Firm*—Cushman, Darby & Cushman IP Group of Pillsbury Madison & Sutro LLP

[57] ABSTRACT

An air-fuel ratio sensor unit including a plate shaped pumping cell 11 with a pin hole 110, a sensing cell 12 including a reference gas chamber 160, a first and a second heating plates 13 and 14 which are arranged to contact with the top and bottom surfaces, respectively, of the pumping cell 11, and a spacer 15 arranged between the first heater 13 and the sensing cell 12. The spacer 15, and the first and the second heater plates 13 and 14 form a passageway for a gas to be detected.

8 Claims, 8 Drawing Sheets

AIR-FUEL RATIO SENSOR UNIT

BACKGROUND OF THE INVENTION

1. Field of the Invention

The present invention relates to an air-fuel ratio sensor unit used for detection of an air-fuel ratio of an air-fuel mixture in an internal combustion engine for an automobile and the like.

2. Description of Related Art

In an internal combustion engine for an automobile and the like, when combustion of an air-fuel mixture is done under a condition that the value of the air-fuel ratio is not in a proper range, the fuel consumption efficiently is reduced, i.e., the loss of the energy of the fuel is increased, and the efficiency of elimination of toxic components in the exhaust gas, which are a cause of air pollution, is reduced.

In view of this, it is necessary to monitor the combustion of the fuel in the internal combustion engine. In order to do this, it is usual to provide an air-fuel ratio sensor in an exhaust pipe of the internal combustion engine for detection of the oxygen density in the exhaust gas discharged from the internal combustion engine. The air-fuel ratio sensor is conventionally constructed by a housing and a sensing unit fixedly arranged in the housing in such a manner that the sensing unit detects the density of the oxygen in the exhaust gas.

In the prior art, the air-fuel ratio sensing unit was constructed by an oxygen pumping cell which was, at its top and bottom surfaces, electrodes and contains a pin hole, a sensing cell having, at its top and bottom, electrodes, a reference gas chamber on one side of the sensing cell, a spacer arranged between the oxygen pumping cell and the sensing cell, a first heater plate which is in contact with the sensing cell, a second heater plate which is in contact with the oxygen pumping cell, and a passageway for the exhaust gas as detected which is formed in the second heater plate and the spacer. These heating plates are each constructed by a substratum plate and a heater on the substratum plate and are for speed-up of the activation of the air-fuel ratio sensor unit and for supplying heat which is lost due to various reason such as a heat conduction, so that the temperature characteristic of the oxygen pumping cell and the sensing cell is compensated.

In order to obtain a desired stable operation of the air-fuel ratio sensor unit, it is required that the temperature of the air-fuel ratio sensor unit should be maintained to a temperature as high as, for example, 700° C.

In the prior art construction, the second heater plate, which is in contact with the oxygen pumping cell, is arranged so that its heater member is in a direct contact with the exhaust gas. However, the temperature of the exhaust gas is dependent from the engine operating condition and varies in a range between 250° to 800° C., which makes it difficult for the air-fuel ratio sensor unit to maintain a desired range of the temperature. Namely, under a condition of a reduced temperature of the exhaust gas, a heat of the sensor unit is removed by the exhaust gas, which causes the temperature measuring characteristic to be varied from the desired one. This problem is made worse when it is considered that the location of the position of the air-fuel ratio sensor unit is varied. Namely, the air-fuel ratio sensor unit is usually located at a lower temperature position away from combustion chambers of an internal combustion engine, which makes it difficult to obtain a stable and precise measuring characteristic.

In the prior art structure, the first heater is in direct contact with the pumping cell, while the second heater is in a direct contact with the sensing cell. This structure provides effective heating of the pumping cell as well as the sensing cell. However, the inventors of this invention have found that the temperature dependency of the pumping cell is much larger than that of the sensing cell.

Furthermore, recently, the range of possible locations of the air-fuel ratio sensor unit is becoming much wider. Namely, it is a recent trend that the air-fuel ratio sensor unit is mounted at a location which is away from the combustion chambers of the internal combustion engine, where the temperature of the exhaust gas is likely to be reduced, which makes the situation worse.

SUMMARY OF THE INVENTION

An object of the present invention is to provide an air-fuel ratio sensor unit capable of overcoming the above-mentioned difficulty in the prior art.

Another object of the present invention is to provide an air-fuel ratio sensor unit capable of maintaining a proper temperature range for a desired characteristic for temperature measurement.

The essence of the invention claimed in claim 1 is in the arrangement of first and second heater plates so that both of them are in contact with the pumping cell at its top and bottom surfaces, respectively. As a result of this arrangement, an uniform heating of the plate shaped pumping cell is obtained at its top and bottom surfaces by the first and second heaters, respectively. Namely, heat generated by both of the first and second heaters can be used for an effective heating of the plate shaped pumping cell. Thus, it becomes possible that the pumping cell is maintained at a temperature which is suitable for detection of the air-fuel ratio.

Advantageously, a heater element of the first or second heater plates is spaced from an outer surface of the sensor unit by a distance of 400 μm or more. As a result, the heat generated from the heater element can be effectively used for heating the pumping cell without being dissipated to the outside atmosphere of the air-fuel ratio sensor unit. It should be noted that a heater located at a distance less than 400 μm from the outer surface of the sensor unit would allow the heat from the heater to be easily dissipated to the atmosphere. Thus, the temperature increase in the sensor unit become insufficient to obtain a stable operation thereof, which makes the precision of the detected air-fuel ratio worse.

Advantageously, a porous member can be arranged in the second passageway. Thus porous member can maintain an amount of gas therein, which functions to suppress the pressure variation of the gas to be detected, thereby obtaining a stable operation of the air-fuel ratio sensor unit.

DESCRIPTION OF PREFERRED EMBODIMENTS

Now, embodiments of the air-fuel ratio sensor according to the present invention will be explained with reference to the attached drawings.

First Embodiment

Figure 1:
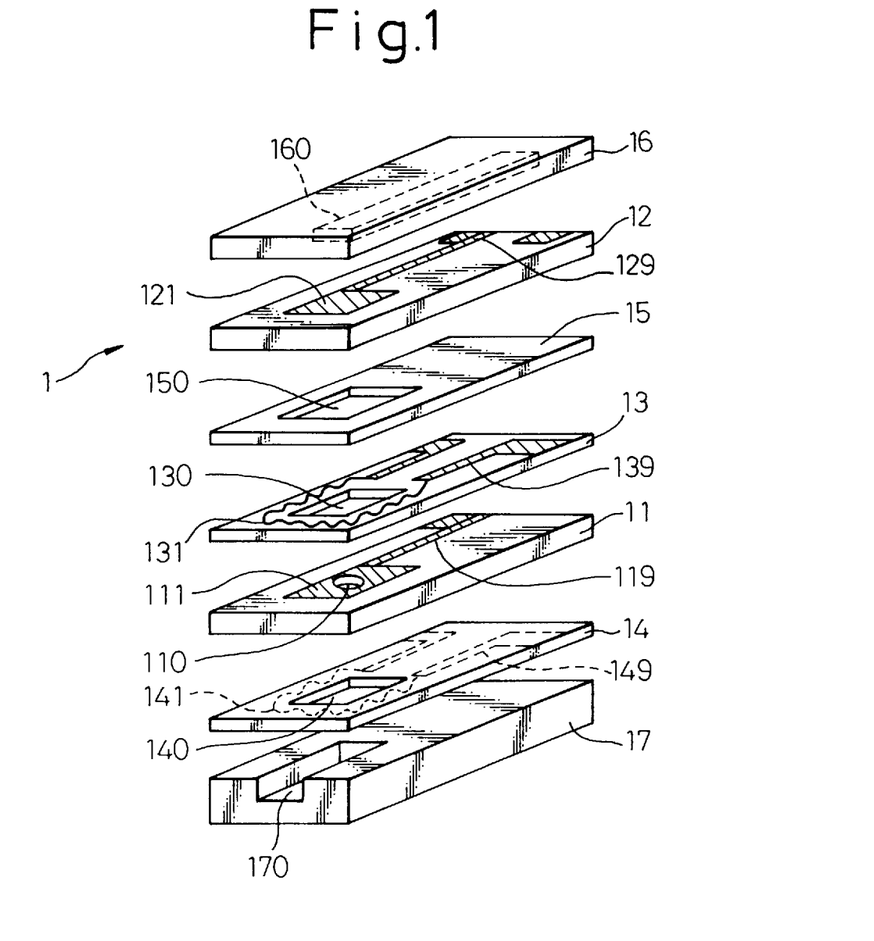
FIG. 1 is a dismantled perspective view of the air-fuel ratio sensor unit according to the first embodiment of the present invention.
Figure 2:
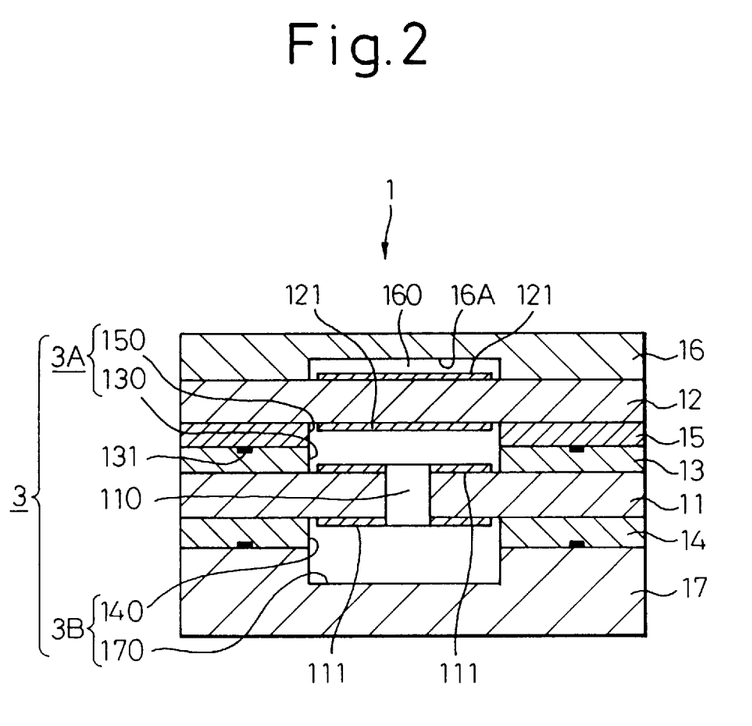
FIG. 2 is a cross sectional view of the air-fuel ratio sensor unit in FIG. 1.
Figure 3:
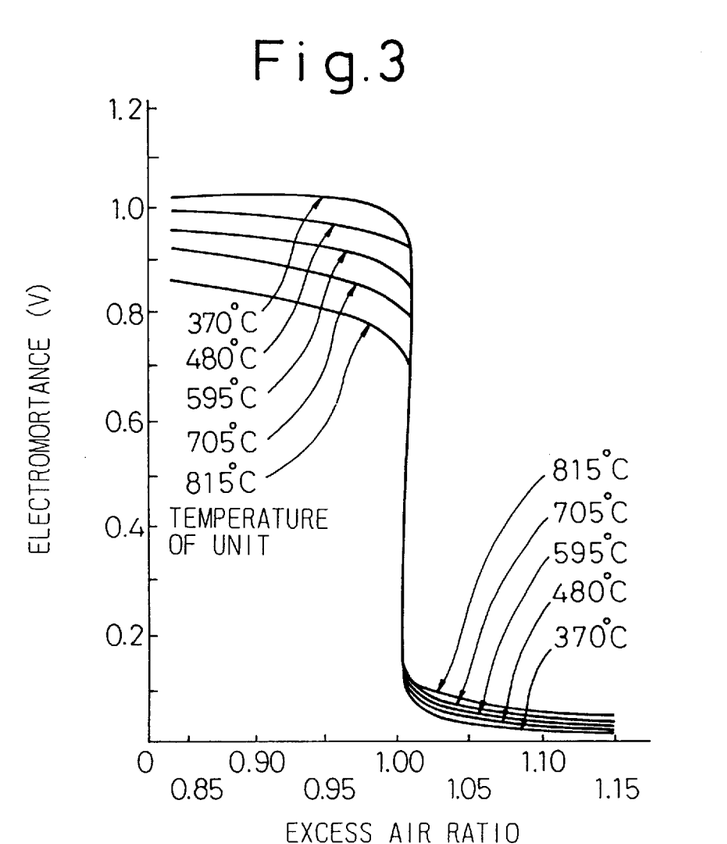
FIG. 3 illustrates relationships between excess air ratios and electromotance (volt).

A first embodiment of an air-fuel ratio sensor unit, as shown in FIGS. 1 to 3, is for detecting an air-fuel ratio of an air-fuel mixture of an internal combustion engine. As shown in FIGS. 1 and 2, the sensor unit 1 includes: an oxygen pumping cell 11 of a plate shape having, at its top and bottom surfaces, electrodes 111, the pumping cell 11 having a pin hole 110 passing therethrough so that the pin hole 110 is opened outwardly at the top and bottom surfaces of the pumping cell 11; a sensing cell 12 of a plate shape having, at its top and bottom surfaces, electrodes 121; first and second heating plates 13 and 14 between which the oxygen pumping cell 11 is sandwiched; a spacer 15 arranged between the sensing cell 12 and the first heating plate 13; a cover cell 16 at the top of the sensing cell 12, and a support plate 17 at the bottom of the second heating plate. As shown in FIG. 2, the cover plate 16 is, at its bottom, formed with an elongated recess 16A, which faces the top surface of the sensing cell 12, thereby creating a reference gas chamber 160, so that a reference gas in the reference gas chamber 160 is in contact with the electrode 121 on the upper surface of the sensing cell 12. As shown in FIG. 1, the spacer 15, the first heating plate 13, and the second heating plate 14 form aligned openings (partition chambers) 150, 130 and 140, respectively, of a rectangular shape. The openings 150 and 130 form an upper measured gas passageway (partition chamber) 3A, which is in contact with the electrode 121 on the lower surface of the sensing cell 12 and the electrode 111 on the upper surface of the pumping cell 11. The support plate 17 forms, at its upper surface, a recess 170, which, together with the opening 140 of the second heating plate 14, form a lower measured gas passageway 3B. The upper and the lower measured gas passageways 3A and 3B, which in combination form a gas introduction passageway 3, are in communication with each other via the pin hole 110.

As schematically shown in FIG. 1, the first heating plates 13 and 14 are formed with heaters 131 and 141, respectively. In this embodiment, the heaters 131 and 141 are spaced from respective outer surfaces of the sensor unit at a distance of 500 μm.

As shown in FIG. 2, the air-fuel ratio sensor 1 is constructed as a laminated structure of the above mentioned various elements, i.e. the cover cell 16, the sensing cell 12, the spacer 15, the first heating plate 13, the plate shaped oxygen sensor cell 11, the second heating plate 14 and the supporting plate 17. Now, details of the construction of these elements will now be explained.

The pumping cell 11 is formed by a plate shaped member of a solid state electrolyte, having a conductivity for an oxygen ion such as one based on a zirconia, and forming a top and bottom surfaces, on which the electrodes 111 made of a porous platinum material are formed. As shown in FIGS. 1 and 2, the electrodes 111 form central openings which are ends of the pin hole 110. Formed integrally to the electrodes 111 are lead electrodes 119, which are for connection to an outside circuit (not shown) such as an air-fuel ratio control circuit which receives an output from the sensor indicating the detected oxygen density.

The sensing cell 12 is, similar to the oxygen pump cell 11, formed of a plate shaped member of a solid state electrolyte, having a conductivity for an oxygen ion such as one based on a zirconia, and forming a top and bottom surfaces on which the electrodes 121 made of a porous platinum material are formed. As in the oxygen pump cell 11, lead electrodes 129 are integrally formed on the electrodes 121.

The first heating plate 13 is formed as a plate made of an electric insulating ceramic material, on which a heater portion 131 for generating a heat when electrically energized as well as a lead electrode portion 139 for feeding an electric power to the heater portion 131 are formed. Similarly, the second heating plate 14 is formed as a plate made of an electric insulating ceramic material, on which a heater portion 141 for generating a heat when electrically energized as well as a lead electrode portion 149 for feeding an electric power to the heater portion 131 are formed.

The heater portion 131 and the lead electrode portion 139 are formed on a surface of the first heating plate 13 facing the spacer 15, while the heater portion 141 and the lead electrode portion 149 are formed on a surface of the second heating plate 14 facing the supporting member 17, thereby obtaining an electrical insulation of the first and second heating plates 13 and 14 with respect to the plate shaped oxygen pumping cell 11.

As shown in FIG. 1, in the first heating plate 13, the heater portion 131 is arranged around the opening 130. Similarly, in the second heating plate 14, the heater portion 141 is arranged around the opening 140. The heater portions 131 and 141 are formed at locations spaced inwardly from the adjacent outer surfaces at a distance of 500 μm.

The spacer plate 15 having the opening 150 is made as a ceramic plate of the same shape as that of the first and second heating plates 13 and 14. As explained above, the electrode 121 at the lower side of the sensing cell 12 is opened to the opening 150.

The cover cell 16 having the recess 16A forming the reference gas chamber 160 is formed as a ceramic plate and the electrode 121 at the upper side of the sensing cell 12 is opened to the recess 16A.

The support member 17 having recess 170 is formed as a ceramic plate as similar to the cover cell 16. It should be noted that the thickness of the supporting member 17 must be 500 μm or more, which allows the heater portion 141 to be located at a distance of 500 μm inwardly from the outer surface of the sensor unit 1.

Now, an operation of the oxygen sensor according to the first embodiment of the present invention will be explained. The sensing cell 12 of this embodiment functions as an oxygen concentration cell, wherein an electromotance is determined in accordance with the partial pressure of the oxygen in the detected gas introduction passageway 3 and the reference chamber 160.

Based on the electromotance, an oxygen concentration in the detected gas, i.e., an exhaust gas of an internal combustion engine for an automobile is detected. From the detected oxygen concentration, an air-fuel ratio of the exhaust gas can be known.

When the air-fuel ratio sensing unit 1 according to the present invention is located in the atmosphere of the exhaust gas, a electromotance is generated in the sensing cell 12 due to the catalytic function of platinum electrodes 121. The value of the electromotance is varied in accordance with an excess air ratio of the exhaust gas, which is the air-fuel ratio of the exhaust gas to be detected divided by the theoretical air-fuel ratio (stoichiometric air-fuel ratio). FIG. 3 shows a relationship between the excess air ratio and the electromotance. The value of the excess air ratio of 1.0 corresponds to the theoretical air-fuel ratio.

As will be seen from FIG. 3, so-called λ characteristic is obtained at an area of the value of the excess air ratio which is adjacent to the value of 1.0. Namely, at a value of the excess air ratio which is equal to or near to 1.0, a sharp change in the value of the electromotance is occurred, regardless of a change in the value of the temperature of the gas to be detected. Contrary to this, at the area of the excess air ratio, which is larger than or smaller than 1.0, there is a temperature dependency of the value of the electromotance.

In view of the above, the value of the excess air ratio kept to or near to 1.0 can maintain the electromotance to be unchanged even when there is a temperature change. As a result, a detection of the air-fuel ratio based on the electromotance can be done without being influenced by the change in the temperature characteristic of the sensing cell 12.

On the other hand, a pumping-in or pumping-out amount of the oxygen ions at the plate shaped pumping cell 11, i.e., an electric current $I_p$ (oxygen pumping current) generated by the pumping cell is determined by the following equation.

$$I_p \cong n \times \frac{F}{R} \times T \times P \times D \times \frac{A}{1} \times X,$$

where n: number of electrons at the electrode reaction;
T: absolute temperature: effective area of the partition chamber
F: Faraday's constant
P: gas pressure
l: effective diffusion length at the partition chamber
R: gas constant
D: diffusion coefficient of component gas
X: concentration of component gas In the above equation, the component gas means the gas to be measured. In view of the above equation, it will be understood that the magnitude of the pumping current depends on the absolute temperature T of the plate shaped pumping cell 11. Thus, it is considered that the temperature of the plate shaped pumping cell 11, which is maintained to a constant value, is indispensable for obtaining a stable operation of the air-fuel ratio sensor unit 1.

In the air-fuel sensor unit 1 according to the present invention, the first and second heating plates 13 and 14 are under a face to face contacted condition with the plate shaped oxygen pumping cell 11 at its top and bottom surfaces, respectively. As a result, the first and second heating plates 13 and 14 can uniformly heat the top and bottom surfaces of the plate shaped oxygen pumping cell 11.

Furthermore, the heater parts 131 and 141 in the first and second heating plates 13 and 14, respectively are spaced at a distance of 400 μm or more from the outer surface of the air-fuel ratio sensor unit 1. As a result, the heat generated from the first and second heating plates 13 and 14 are effectively used for heating the plate shaped oxygen pumping cell 11 without being emitted to the outside of the air-fuel ratio sensor unit 1. As a result, the construction of the present invention allows the plate shaped oxygen pumping cell 11 to be effectively maintained at a temperature which is the most suitable for the detection of the air-fuel ratio.

In short, according to the first embodiment of the present invention, it is possible that the air-fuel ratio sensor is one that can always keep a suitable temperature of the plate shaped oxygen pumping cell for executing an air-fuel ratio detection.

Now, a result of a test is explained for a determination of a desired value of the distance of the heater part from the outer surface of the air-fuel ratio sensing unit.

First, six samples of air-fuel ratio sensing units of a first type were prepared, which have the same construction as that in the first embodiment having the first and second heater portions 13 and 14. For both of the heater portions, the distances from the outer surface of the samples were, respectively, 100 μm, 200 μm, 300 μm, 400 μm, 500 μm and 600 μm.

Furthermore, six samples of air-fuel ratio sensing units of a second type were also prepared, which have the same construction as that in the first embodiment, except that only one heating part 13 or 14 is provided. The distances of the heater part from the outer surface of the samples were, respectively, 100 μm, 200 μm, 300 μm, 400 μm, 500 μm and 600 μm.

The test was done in the following way. Each of the above six samples for each of the first and second types is mounted on an evaluation bench located in an internal combustion engine, in such a manner that an exhaust gas from the engine contacts the sample. The temperature of the exhaust gas was 400° C. and the flow amount of the exhaust gas was 5 liters per minute. The temperature of the air-fuel ratio sensing unit heated by the electric first and second heating plates were kept to 700° C. Then, the pumping-in or pumping-out of the oxygen gas as the pumping cell 11 was controlled in such a manner that the output voltage at the sensing cell 12 becomes 0.45 volt. An output current of the pumping cell 11, which is expressed by $I_p(5)$, was measured.

Then, the flow amount of the exhaust gas was increased to 50 liters per minute, while maintaining other conditions unchanged. Then, the measurement of the output current of the pumping cell 11, which is expressed by $I_p(50)$, was also done. Based on the measured values of the output currents $I_p(5)$ and $I_p(50)$, a characteristic changing ratio, which is expressed by:

$$\frac{I_p(5) - I_p(50)}{I_p(5)} \times 100\ (\%)$$

is calculated.

Figure 4:
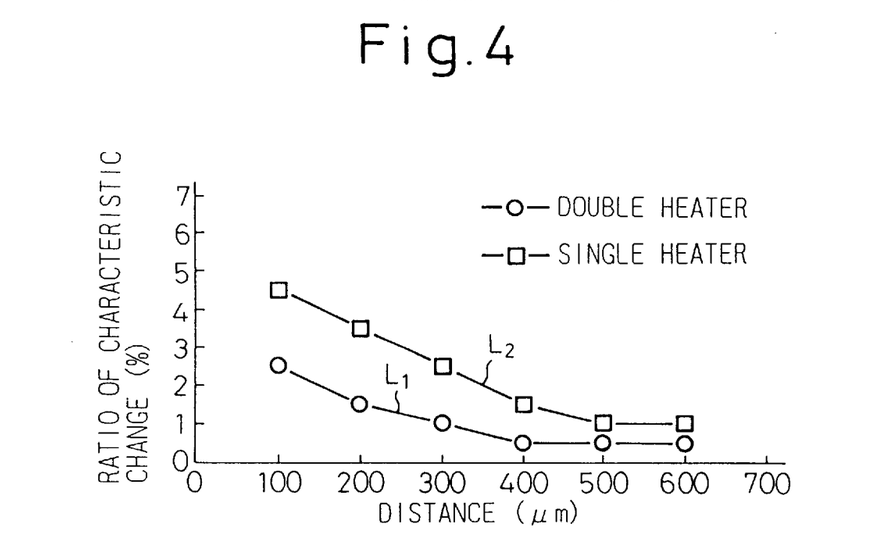
FIG. 4 illustrates relationships between the distances from the sensor surface and characteristic change ratios.

FIG. 4 shows the result of the test. Namely, in FIG. 4, the abscissa indicate, the distance (μm) of the heater portion from an outer surface of the air-fuel ratio sensing unit, while an ordinate indicates the characteristic changing ratio (%). A line $L_1$ shows the result of the test for the first type samples having two heater portions, while a line $L_2$ shows the result of the test for the second type sample having only one heater portion. As can be understood from FIG. 4, the samples in the first type having two heaters (first and second heating plates 13 and 14) can obtain a reduced value of the characteristic changing ratio when compared with the samples in the second type having only one heater. As can also be understood from FIG. 4, an arrangement of the heater portions at a location at a distance from the outer surface, which is longer than 400 μm, causes the reduction in the characteristic changing ratio to be unchanged (saturated).

In short, it has been proved that the provision of the first and second heating plates 13 and 14 arranged inwardly at a distance of 400 μm from the outer surface can obtain a stabilized air-fuel ratio measurement characteristic of the air-fuel ratio sensing unit.

Second Embodiment

Figure 5:
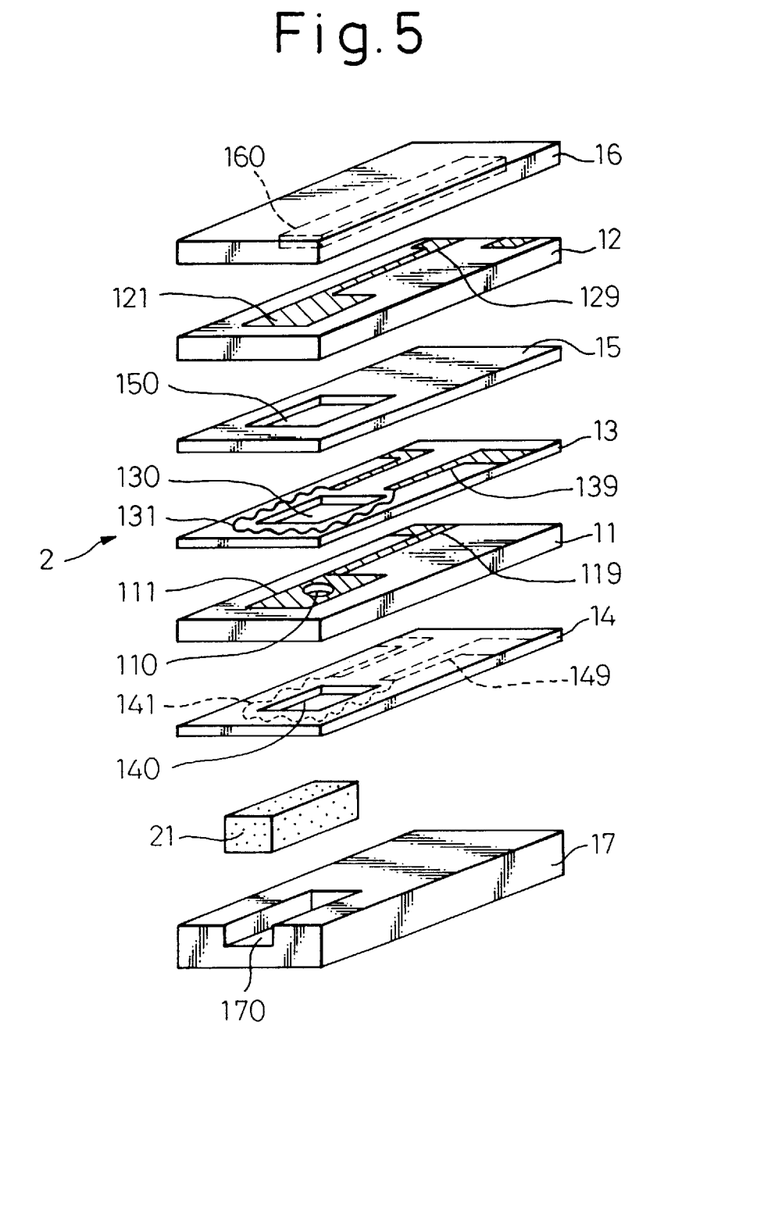
FIG. 5 shows a dismantled perspective view of the air-fuel ratio sensor unit according to the second embodiment of the present invention.
Figure 6:
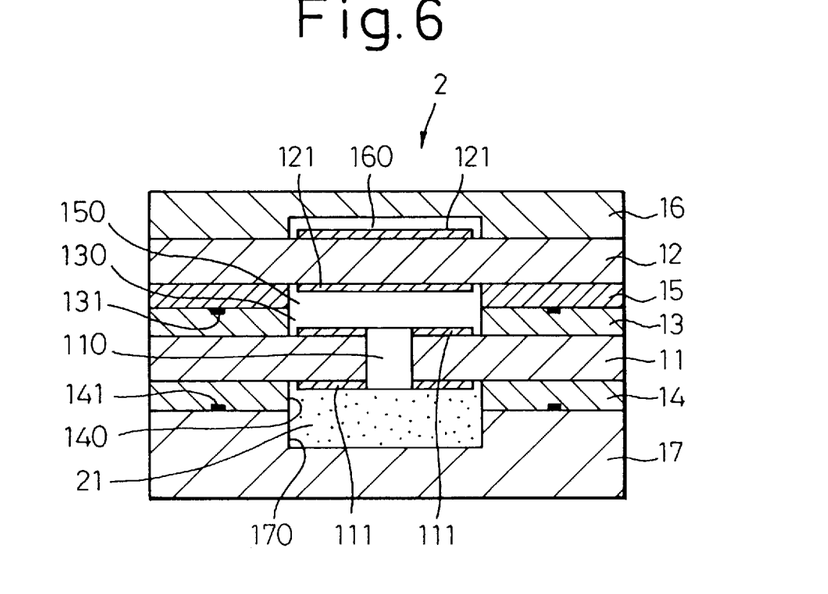
FIG. 6 is a cross sectional view of the air-fuel ratio sensor unit in FIG. 5.

An air-fuel ratio sensor unit in second embodiment shown in FIGS. 5 and 6 features the provision of a porous member.

In addition to a plate shaped pumping cell 11, a sensing cell 12, a spacer 15 for formation of a partitioned chamber, a first and second heating plates 13 and 14, a cover cell 16 and a supporting plate 17, the air-fuel ratio sensor unit of this embodiment includes a porous (gas holding) member 21 made of a porous material such as alumina, which is fitted to a recess 170 on the supporting plate 17 and an opening (partition chamber) 140 in the second heating plate 14. The porous member 21 is located at the inlet passageway for the exhaust gas to be detected.

As explained above, the measuring characteristic of the plate shaped pumping cell 11 is also dependent on the pressure of the gas to be detected as will be understood from the above mentioned equation as to the pumping current $I_p$. In this embodiment, an amount of exhaust gas can be held in the porous member 21, which functions as a buffer for cancelling a variation of the pressure of the gas. This pressure variation cancelling operation of the porous member 21 allows the measuring characteristic of the plate-shaped pumping cell to be stabilized.

In place of an alumina for constructing the porous member 21, another ceramic material such as spinel or steatite can be employed.

Now, a result of a test of the provision of the porous member will be explained. A sample of the air-fuel ratio sensor unit as shown in FIGS. 5 and 6 and a sample of the same structure except that no porous member was provided, were prepared.

Figure 7:
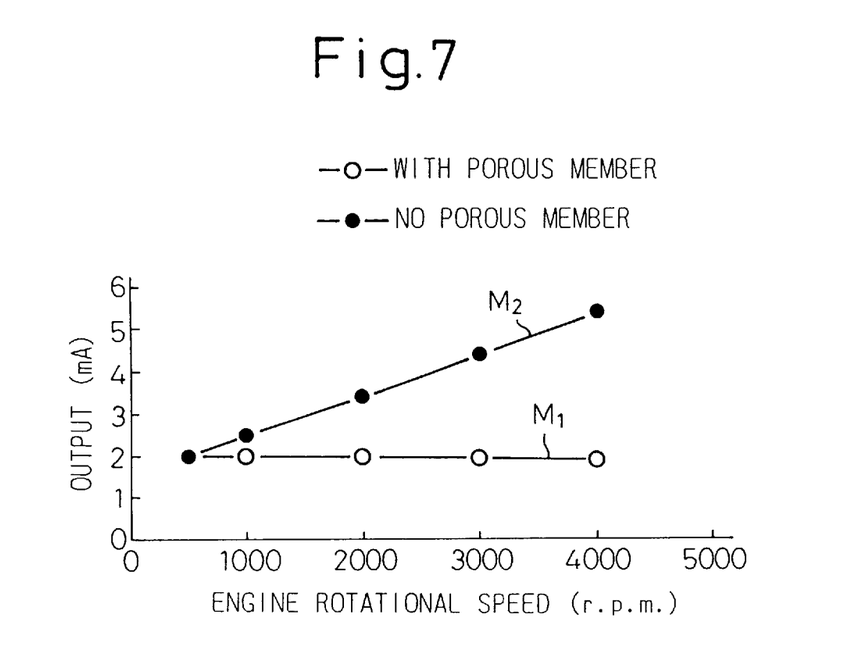
FIG. 7 illustrates relationships between an engine rotating speed and an output current of the air-fuel ratio sensor unit.

Each of the above two samples was mounted to an exhaust pipe of an internal combustion engine. Then, the engine is operated under various rotating speed in a range between 500 to 4,000 r.p.m., while an output of the air-fuel ratio sensor unit is measured in the similar way as explained with reference to FIG. 3. The result of this test is shown in FIG. 7, in which the abscissa indicates a rotating speed (r.p.m.) of the internal combustion engine and the ordinate indicates an output current (mA) of the air-fuel ratio sensor unit. A curve $M_1$ shows a relationship between the output current and the output current of the air-fuel ratio sensor unit having the porous layer, while a curve $M_2$ shows a relationship between the output current and the output current of the air-fuel ratio sensor unit with no provision of the porous layer. As easily understood from FIG. 7, a substantially constant output current with respect to the change in the engine rotating speed is obtained for the air-fuel ratio sensor unit with the porous member 21 as shown by the curve $M_1$. Contrary to this, when such a porous member is not provided, the output current increases as the engine rotating speed increases as shown by the curve $M_2$. Namely, the increase in the engine rotating speed causes a pulsation of the pressure of the exhaust gas to be generated due to a variation between engine cylinders. The provision of the porous layer which can function as a buffer cancels the pulsation of the pressure, thereby obtaining an output current which is independent from the change in the engine rotating speed. Contrary to this, when the sensor is not provided with the porous layer, the pulsation of the exhaust gas causes the pumping current to be changed in accordance with the above mentioned equation, which causes the precision of the measurement of the air-fuel ratio to be reduced.

Modifications

Now, modifications of this embodiment will be explained.

Figure 8:
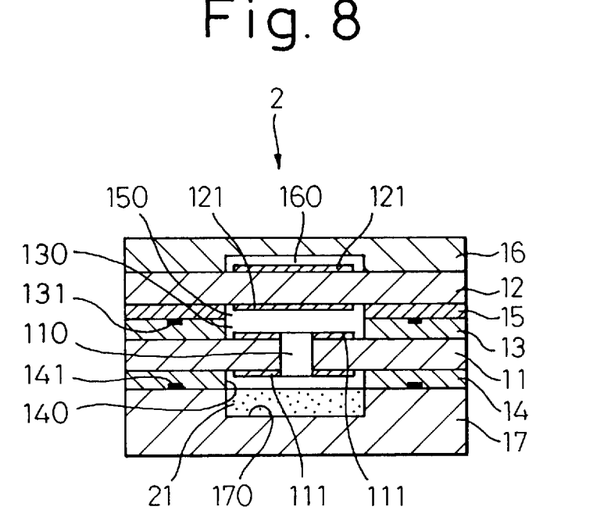
FIG. 8 is a cross sectional view of the air-fuel ratio sensor unit in a modification.

As shown in a modification in FIG. 8, the porous layer 21 can be arranged only in the recess 170 of the supporting plate 17.

Figure 9:
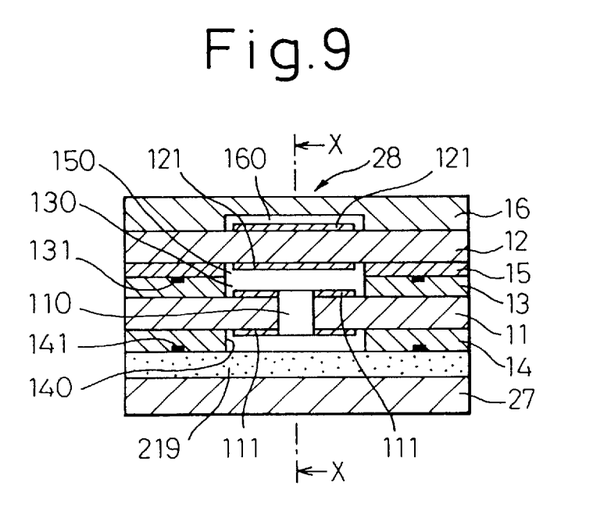
FIG. 9 is a cross sectional view of the air-fuel ratio sensor unit in another modification.
Figure 10:
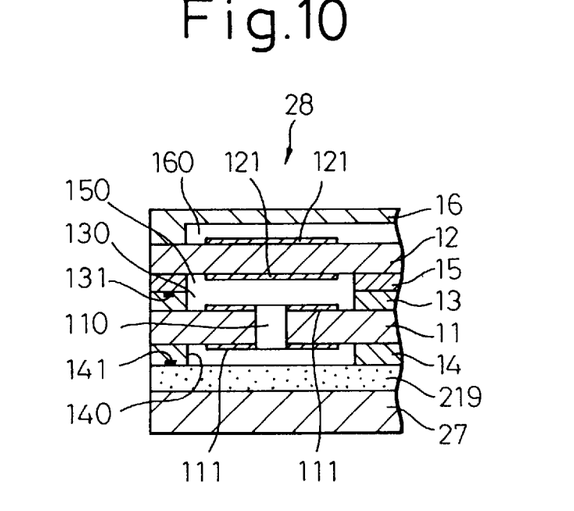
FIG. 10 is a cross sectional view taken along line X—X in FIG. 9.

In a modification of the embodiment with the porous layer shown in FIGS. 9 and 10, in place of recessed supporting plate 17 in FIGS. 5 and 6, a supporting member 27 with no recess is provided, and a porous plate 219, which extends along the entire length and the width of the air-fuel ratio sensor unit, is arranged between the supporting member 27 and the second heating plate 14.

Figure 11:
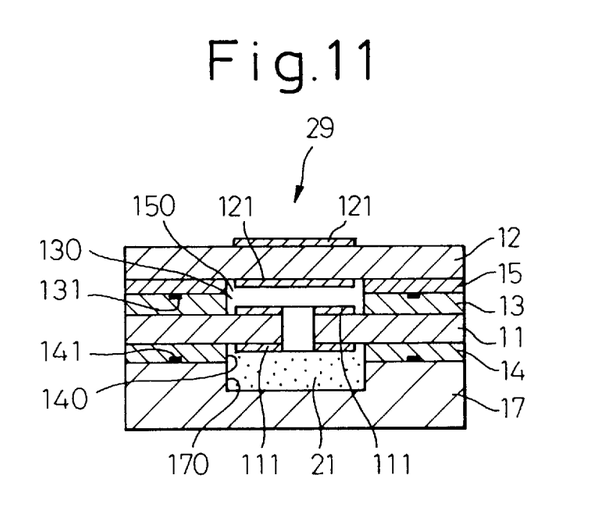
FIGS. 11 and 12 are, respectively, cross sectional views of the air-fuel ratio sensor unit in further other modifications.

In another modification in FIG. 11, the construction is the same as the embodiment in FIGS. 5 and 6, except that the cover plate 16 is eliminated.

Figure 12:
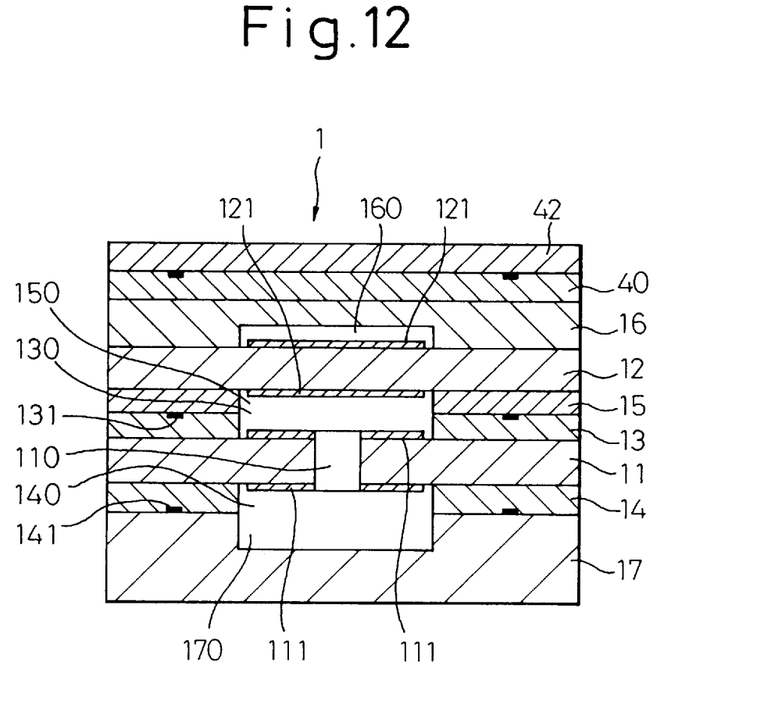

In a modification shown in FIG. 12, in addition to the first and second heating plates 13 and 14, a third heating plate 40 as well as a cover plate 42 are provided at the top of the air-fuel ratio sensor unit. The remaining construction is the same as that in FIGS. 1 and 2. The provision of the third heating plate is desirable in that it provides improved stability as well as increased precision.

We claim:

1. An air-fuel ratio sensor unit comprising:

an oxygen pumping cell of a plate shape having a pin hole and forming a pair of electrodes;

a first heater plate located on one side of the oxygen pumping cell, while forming a first passageway;

a second heater plate located on the other side of the oxygen pumping cell, while forming a second passageway;

the first and second passageways being in communication with each other via the pin hole for a passage of a gas to be detected;

a sensing cell located on one side of the first heater plate remote from the oxygen pumping cell and having a reference gas chamber; and a spacer located between the first heater plate and the sensing cell, said first and second heater plates being arranged with the oxygen pumping cell therebetween such that the temperature of the oxygen pumping cell remains constant irrespective of changes in heat of the gas to be detected.

2. An air-fuel ratio sensor unit according to claim 1, wherein each of said heater plates is formed with a heater element, which is spaced from an outer surface of the sensor unit at a distance of 400 μm or longer.

3. An air-fuel ratio sensor unit according to claim 1, and further comprising a porous member arranged in the second passageway.

4. An air-fuel ratio sensor unit according to claim 1, further comprising a top cover located on one side of the sensing cell spaced from the pumping cell, the reference gas chamber being formed between the top cover and the sensing cell.

5. An air-fuel ratio sensor unit according to claim 1, further comprising an additional heater plate arranged on the side of the sensing cell remote from the pumping cell.

6. An air-fuel ratio sensor unit comprising:

an oxygen pumping cell of a plate shape having a pin hole and forming a pair of electrodes;

a first heater plate located on one side of the oxygen pumping cell, while forming a first passageway;

a second heater plate located on the other side of the oxygen pumping cell, while forming a second passageway;

the first and second passageways being in communication with each other via the pin hole for a passage of a gas to be detected;

a sensing cell located on one side of the first heater plate remote from the oxygen pumping cell and having a reference gas chamber;

a spacer located between the first heater plate and the sensing cell, and;

a support plate on which said second heater plate is mounted, the support plate being formed with a recess which opens to the second passageway for introduction of the detected gas.

7. An air-fuel ratio sensor unit according to claim 6, and further comprising a porous member which is arranged in said recess.

8. An air-fuel ratio sensor unit according to claim 6, and further comprising a porous member which is arranged in the second passageway as well as in the recess.

* * * * *